United States Patent
Stouffer et al.

(12)

(10) Patent No.: US 6,239,300 B1
(45) Date of Patent: May 29, 2001

(54) METALLOCENE PRODUCTION PROCESS

(75) Inventors: Carleton E. Stouffer; Syriac J. Palackal, both of Bartlesville; Gary L. Glass, Dewey; M. Bruce Welch, Bartlesville; John D. Hottovy, Bartlesville; Michael D. Jensen, Bartlesville, all of OK (US)

(73) Assignee: Phillips Petroleum Company, Bartlesville, OK (US)

( * ) Notice: Subject to any disclaimer, the term of this patent is extended or adjusted under 35 U.S.C. 154(b) by 0 days.

(21) Appl. No.: 09/251,564

(22) Filed: Feb. 17, 1999

(51) Int. Cl.$^7$ ................. C07F 17/00; C07F 7/00
(52) U.S. Cl. ................. 556/53; 585/354; 987/2; 502/103; 502/117; 526/160; 526/943
(58) Field of Search ................. 585/354; 556/53; 987/2; 502/103, 117; 526/160, 943

(56) References Cited

U.S. PATENT DOCUMENTS

| | | | |
|---|---|---|---|
| 3,772,396 | * 11/1973 | Boesenbrg et al. | 260/666 A |
| 5,498,581 | 3/1996 | Welch et al. | 502/102 |
| 5,565,592 | 10/1996 | Patsidis et al. | 556/11 |
| 5,616,752 | 4/1997 | Patsidis et al. | 556/95 |

* cited by examiner

*Primary Examiner*—Porfirio Nazario-Gonzalez
(74) *Attorney, Agent, or Firm*—Edward L. Bowman

(57) ABSTRACT

A number of process steps are provided that can be combined to produce bridged cyclopentadienyl-fluorenyl metallocenes. The process steps include production of a cyclopentadiene compound from dicyclopentadiene; production and recovery of a fulvene compound using the cyclopentadiene compound; production of a raw metallocene product using the fulvene compound; and recovery of the pure metallocene from the raw product.

42 Claims, 4 Drawing Sheets

METALLOCENE PRODUCTION PROCESS

The invention relates to metallocenes and in particular to a process for producing a bridged cyclopentadienyl-fluorenyl metallocene.

A bridged cyclopentadienyl-fluorenyl metallocene has a cyclopentadienyl group and a fluorenyl group bound together by a structural bridge. In its most preferred form, the structural bridge has a branch characterized by olefinic unsaturation. These types of metallocenes have been found to be very effective in catalyst systems for the polymerization of olefins. Heretofore, however, processes for producing such metallocenes have been relatively rudimentary and impractical for commercial implementation. It is one thing to prepare bench scale quantities of such metallocenes. It is another to design a process capable of using readily available materials to produce large commercial scale quantities of such metallocenes in a safe and effective manner.

It is, therefore, an object of the invention to provide an improved process for producing a bridged cyclopentadienyl-fluorenyl metallocene which lends itself to commercial implementation.

Another object of the present invention is provide processes for preparing commercial scale quantities of the various intermediates needed to prepare such metallocenes.

In a particularly preferred embodiment, an object of this invention is to provide a process for producing a commercially viable process for producing metallocenes of the type covered by claim 3 of U.S. Pat. No. 5,565,592 as well as metallocenes of the type described in claim 13 of U.S. Pat. No. 5,498,581. The disclosures of those patents is hereby incorporated by reference.

SUMMARY OF THE INVENTION

In accordance with one embodiment of the present invention a bridged cyclopentadienyl fluorenyl metallocene is produced by (1) reacting a fluorene compound with an alkyl lithium in a liquid consisting essentially of a non-cyclic ether, alkane, or mixtures thereof to form the fluorenyl lithium salt, (2) adding an unsubstituted or hydrocarbyl substituted fulvene to the reaction mixture of step (1) to produce a lithium salt of an organic compound in which fluorenyl and cyclopentadienyl radicals are connected by a single carbon atom, (3) adding additional alkyl lithium to produce the dilithium salt of the organic compound, (4) forming a liquid mixture of a transition metal compound selected from the group consisting of the tetrahalides of Ti, Zr, and Hf by combining the transition metal compound with an liquid alkane and non-cyclic ether, (5) combining the liquid mixture with the product of step (3) to form the metallocene, and (6) separating the metallocene from the reaction product.

In accordance with another embodiment of the present invention there is provided a process for producing a bridged cyclopentadienyl fluorenyl metallocene by (1) passing dicyclopentadiene into a wiped film evaporator under conditions suitable for effecting cracking of the dicyclopentadiene to cyclopentadiene vapor, (2) distilling the reaction product and recovering cyclopentadiene, (3) reacting the recovered cyclopentadiene with a carbonyl compound selected from hydrocarbyl substituted ketones and hydrocarbyl substituted aldehydes in the presence of methanol and an organic base to produce a 6-hydrocarbyl substituted fulvene, preferably a 6-omega alkenyl fulvene, (4) adding a liquid alkane to the product of step (3) and subjecting the resulting mixture to separation in a liquid/liquid extraction column using water as the continuous phase, (5) recovering the 6-hydrocarbyl substituted fulvene from the alkane phase, (6) reacting a fluorene compound with an alkyl lithium in a liquid consisting essentially of non-cyclic ether, alkane, or mixtures thereof to form the fluorenyl lithium salt, (7) adding the 6-hydrocarbyl substituted fulvene to the reaction mixture of step (6) to produce a lithium salt of an organic compound in which fluorenyl and cyclopentadienyl radicals are connected by a single carbon atom, (8) adding additional alkyl lithium to produce the dilithium salt of the organic compound, (9) forming a liquid mixture of a transition metal compound selected from the group consisting of the tetrahalides of Ti, Zr, and Hf by combining the transition metal compound with an liquid alkane and non-cyclic ether,

(10) combining the liquid mixture with the product of step (8) to form the metallocene, and

(11) separating the metallocene from the reaction product.

In accordance with another aspect of the invention there is provided a method for producing cyclopentadiene from dicyclopentadiene comprising cracking the dicyclopentadiene in a wiped film evaporator.

In accordance with another aspect of the invention a fulvene is reacted with the lithium salt of a fluorene compound to produce a an organic compound in which a cyclopentadienyl radical and a fluorenyl radical are connected to each other by a single carbon atom, adding acid and a hydrocarbon to the reaction mixture, and passing the resulting mixture to a liquid/liquid extraction column containing water, and withdrawing the organic phase from the top of the extraction column and then separating the organic compound from the solvent by evaporation.

In accordance with yet another aspect of the invention there is provided a process for recovering metallocene from a raw product comprising metallocene and alkali metal halide comprising mixing the raw product with a halogenated organic solvent in which the metallocene is soluble and the alkali metal halide is insoluble and then subjecting the mixture to centrifuging to separate the solid alkali metal halide as a solid and then recovering the metallocene from the solvent.

DETAILED DESCRIPTION OF THE INVENTION

The alkyl lithium employed in the present invention can be selected from any suitable alkyl lithium. Generally one would employ an alkyl lithium having 1 to 10 carbon atoms. In a particularly preferred embodiment one employs n-hexyl lithium, which has advantages over lower molecular weight alkyl lithium compounds such as methyl lithium and butyl lithium in that n-hexyl lithium is less flammable. By using hexyllithium, the resulting by-product is hexane, which can simply be left in the third mixture as the above-mentioned second hydrocarbon. According to conventional practice, the use of butyllithium gives off butane gas, which must be vented. Moreover, butyllithium is highly pyrophoric and therefore hazardous. Hexyllithium is less pyrophoric than butyllithium to thereby enhance safety.

The term hydrocarbyl substituted fulvene is used herein to refer to a compound having the structure of fulvene but having at least one hydrocarbyl group on either the cyclic structure or on the terminal carbon of the olefin double bond of the fulvene structure. Typically the hydrocarbyl substituent on the fulvene would be an alkyl group have 1 to 10 carbon atoms or an alkenyl group having 2 to 10 carbon atoms. In a particularly preferred embodiment the hydrocarbyl substituted filvenes are substituted at the 6 position with a terminal alkenyl group. An example would be 6-(3-butenyl)-6-methylfulvene. The organic base used in producing the fulvene can be selected from any suitable organic secondary amine. Pyrrolidine is currently preferred.

In the embodiment wherein a carbonyl compound is reacted with cyclopentadiene to form a 6-hydrocarbyl fulvene, the carbonyl compound is selected from hydrocarbyl substituted ketones and hydrocarbyl substituted aldehydes. Typically the hydrocarbyl groups of the carbonyl compound would have 1 to 10 carbon atoms. In a particularly preferred embodiment the hydrocarbyl group substituent of the carbonyl compound has terminal olefinic unsaturation. An example would be 5-hexene-one.

The term fluorene compound as used herein refers to unsubstituted fluorene as well a compounds in which one or more of the hydrogens of fluorene has been replaced by a hydrocarbyl group, preferably containing 1 to 10 carbon atoms. Examples include fluorene, 1-methylfluorene, 4-methylfluorene, 9-butylfluorene, 5-(4-butenyl)fluorene), 1,2-benzofluorene, 2,3:6,7-dibenzofluorene, 4,5 benzofluorene,and the like. The currently preferred substituents for the substituted fluorene compounds are either alkyl or alkenyl substituents.

The conditions employed in the various steps, such as temperature and pressure, can vary depending upon the particular results that are desired.

It is known in the art that dicyclopentadiene can be cracked to produce cyclopentadiene by heating the liquid dicyclopentadienyl compound in a suitable vessel at a temperature below the boiling point of the dicyclopentadienyl compound but sufficiently high to achieve cracking; however, this cracking technique is time consuming (i.e. hours or even a full day), potentially hazardous to the operator or technician, and results in loss of some of the cyclopentadiene due to polymerization. Moreover, the resulting polymer builds up on the cracking vessel and is extremely difficult to remove. In accordance with the present invention dicyclopentadiene is cracked to cyclopentadiene in a wiped film evaporator. This also for very short residence time and minimizes the lost of cyclopentadiene. The cracking is carried out by passing a liquid form of dicyclopentadienyl into and through the wiped film evaporator under conditions conducive to the vaporization and cracking of the dicyclopentadiene. Typically the cracking is carried out at a temperature in the range of about 170 to about 300° C.

An example of an embodiment of the present invention is realized by a process comprising: (a) passing dicyclopentadiene in liquid form into and through an evaporator under conditions conducive to the vaporization and cracking of the dicyclopentadienyl compound, thereby producing a cyclopentadiene as a vapor; (b) condensing the vaporous cyclopentadiene to a liquid; (c) reacting, in a water-soluble alcohol and in the presence of an organic base, the liquid cyclopentadiene compound with a hydrocarbyl substituted carbonyl compound selected from an aldehyde or a ketone to thereby produce a first mixture containing a fulvene compound; (d) adding an acid and a first hydrocarbon to the first mixture, the acid being reactive with the base to produce a water-soluble salt and the fulvene compound being soluble in the first hydrocarbon to thereby result in a second mixture; (e) passing second mixture to a water-containing extraction column to establish therein a bottom liquid phase, containing the water-soluble salt and alcohol as dissolved in the water, and a top liquid phase containing the fulvene compound as dissolved in the first hydrocarbon; (f) withdrawing top liquid phase from the extraction column and separating the first hydrocarbon from the fulvene compound; (g) reacting a fluorene compound with an alkali metal alkyl in a non-cyclic ether, and then adding thereto the fulvene compound and additional alkali metal alkyl to a result in a third mixture comprising a bridged cyclopentadienyl fluorenyl alkali metal salt in which cyclopentadienyl and fluorenyl radicals are connected by a single carbon atom; (h) providing a second hydrocarbon in the third mixture and separating the non-cyclic ether therefrom to form a fourth mixture having the bridged cyclopentadienyl fluorenyl alkali metal salt as solids in a second hydrocarbon-based liquid comprising the second hydrocarbon with any unreacted fluorene, alkali metal alkyl, and fulvene compound dissolved therein, and then separating the second hydrocarbon-based liquid from the bridged cyclopentadienyl fluorenyl alkali metal salt solids; (i) mixing the bridged cyclopentadienyl fluorenyl alkali metal solids with fresh second hydrocarbon and a zirconium, titanium, or hafnium tetrahalide compound so that the tetrahalide compound reacts with the bridged cyclopentadienyl fluorenyl alkali metal salt to produce a raw product comprising the bridged cyclopentadienyl-fluorenyl metallocene and an alkali metal halide as solids in the second hydrocarbon as a fifth mixture, and then separating the second hydrocarbon from the raw product; (j) mixing the raw product with a halogenated organic solvent in which the metallocene is soluble and the alkali metal halide is insoluble, thereby producing a sixth mixture comprising a metallocene solution and the alkali metal halide solids; and (k) subjecting the sixth mixture to centrifuging so as to separate the alkali metal halide solids from the metallocene solution and then recovering the metallocene as solids from the metallocene solution.

Recovery of the fulvene compound in accordance with steps (d)–(f) is very efficient and can be performed in a continuous manner as discussed further below to result in a fulvene product of high purity.

Production of the raw product in accordance with steps (g)–(I) does not require isolation and recovery of the cyclopentadienyl-fluorenyl ligand as is required by prior art processes. This eliminates time consuming steps to thereby contribute to the efficiency of the inventive process.

In step (k), separation of the alkali metal halide solids from the metallocene solution by centrifuging is a distinct improvement over the conventional technique of silica filtration. Not only is centrifuging more effective in separating the small (submicron) alkali metal halide particles from the metallocene solution, the waste and expense of having to periodically replace old silica with new silica is avoided.

According to a particularly preferred aspect of the invention, the alkali metal alkyl as used in step (g) is hexyllithium.

Other preferred components for use in the invention are as follows: dicyclopentadiene compound—unsubstituted dicyclopentadiene; carbonyl compound—an olefinic carbonyl compound such as 5-hexen-2-one; alcohol—methanol; base—a secondary amine such as pyrrolidine; acid—a weak acid such as acetic acid; first hydrocarbon—an alkane such as pentane; fluorene compound—unsubstituted fluorene; second hydrocarbon—an alkane such as hexane; non-cyclic ether—an alkyl ether such as diethylether; tetrahalide compound—zirconium tetrachloride.

According to other aspects of the invention, the overall process described above can be separated into process subcombinations relating to the production of a cyclopentadiene compound, production and recovery of a fulvene compound, production of a raw metallocene product, and recovery of a pure metallocene from a raw metallocene product.

DESCRIPTION OF A PREFERRED EMBODIMENT

The preferred embodiment, as described below, gives some specific parameters such as volumes, temperatures, times, etc. Such specific parameters are provided only by way of example, and should not be construed to limit the invention in any manner.

In the following description, the term "jacketed" as applied to any piece of equipment means that it has a temperature control jacket for either heating or cooling purposes. The term "jacketed mixing vessel" means a vessel having a temperature control jacket as well as a mechanism for mixing the contents of the vessel. It should further be understood that the respective systems shown in FIGS. 1–4 are purged with a suitable inert gas, such as nitrogen, prior to operation, and each system is generally maintained at a pressure slightly above atmospheric pressure (i.e. 1 or 2 psig) to keep out air and moisture as contaminants to the process. Higher pressures (up to about 30 psig) are used at certain points of the process where noted.

Figure 1:
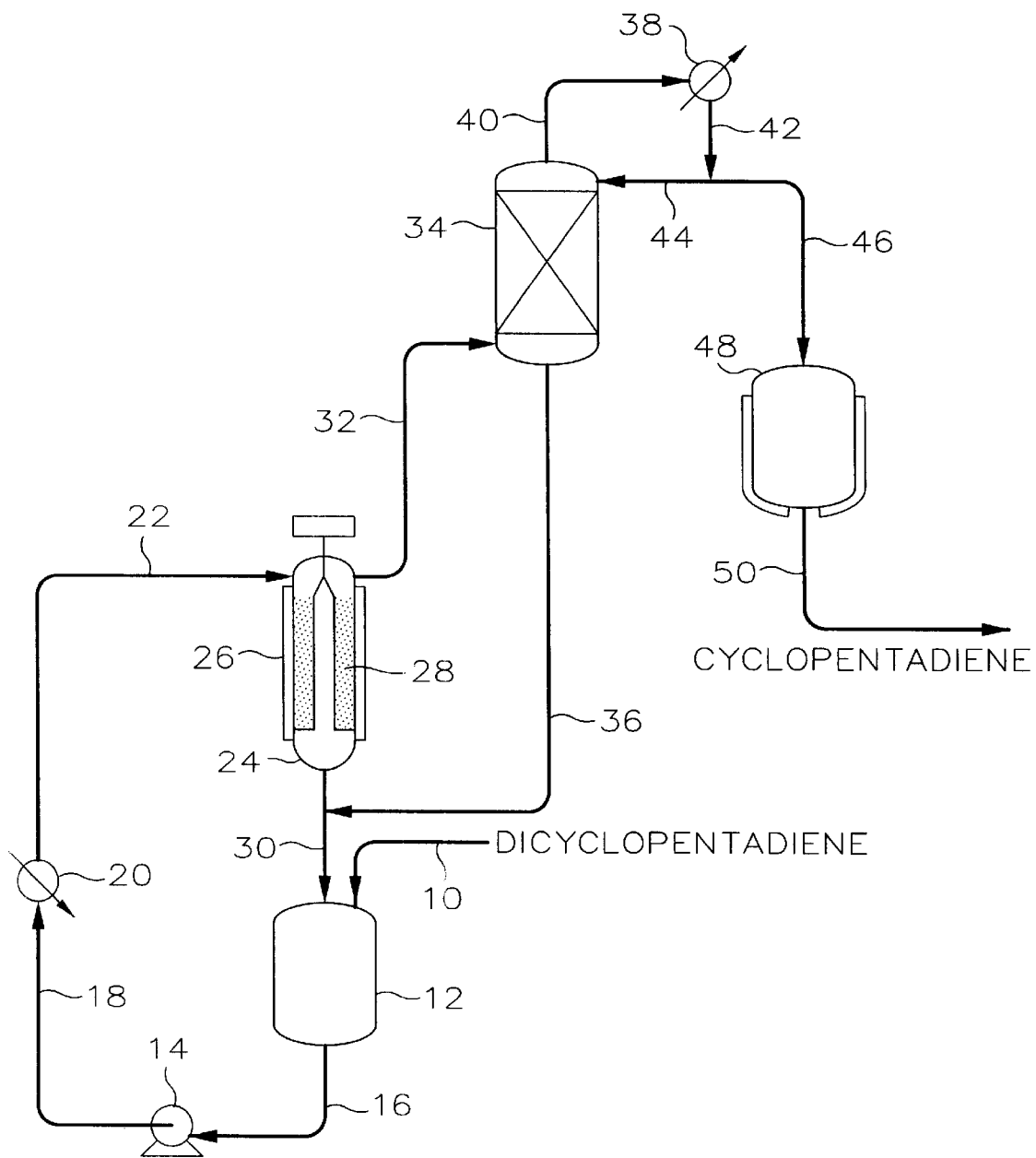
FIGS. 1–4 are schematic flow diagrams illustrating different stages of the described preferred embodiment. Such diagrams are highly simplified, and should be understood to omit details such as valves and other control mechanisms well known to those skilled in the art of process control.

Referring to FIG. 1, dicyclopentadiene (unsubstituted) is charged in liquid form through line 10 into vessel 12. Dicyclopentadiene can be in "liquid form" at ambient temperature as a highly concentrated (i.e. 95 weight percent) solution using a high boiling point solvent such as toluene or xylene. Such liquid dicyclopentadiene is commercially available. Pump 14 pumps the liquid dicyclopentadiene from vessel 12, through line 16, and through line 18 to preheater 20. Preheated liquid dicyclopentadiene flows through line 22 to wiped film evaporator 24.

Wiped film evaporator 24 has at least one heating band 26, and also has a plurality of wipers 28 (preferably carbon) which contact its inner surface. Wipers 28 are rotated by a suitable motor, typically at about 100–300 RPM. As wiped film evaporator 24 receives the flow of liquid dicyclopentadiene via line 22, the rotating wipers maintain a thin (i.e. about 1 mm) liquid film on the evaporator's inner surface. Conditions in wiped film evaporator 24 are conducive to the vaporization and cracking of the liquid dicyclopentadiene to cyclopentadiene. Such conditions include a typical pressure of about 1–2 psig and a preferred temperature of about 170–300° C., most preferably about 200–250° C. The upper temperature limits are dictated primarily by the melting temperature of seals around a drive shaft extending between the motor and the wipers. Very small amounts of vaporous dicyclopentadiene which fail to crack and then condense are allowed to flow from the bottom of wiped film evaporator 24, through line 30, and into vessel 12.

Vaporous cyclopentadiene flows from wiped film evaporator 24 as overhead product through line 32 and into the bottom of distillation column 34. If desired, line 32 can have an internal or external heater (not shown), preferably at a temperature of about 400–500° C., to enhance cracking efficiency by cracking vaporous dicyclopentadiene not cracked in wiped film evaporator 24. Distillation column 34, having an internal pressure of about 1–2 psig, preferably has an overhead temperature of about 45° C. Such conditions cause the condensation of any uncracked dicyclopentadiene and its associated solvent, which as bottoms product, flows through line 36 and then into and through line 30 to vessel 12. Vaporous cyclopentadiene flows as overhead product to condenser 38 via line 40. Condenser 38 (set at 0° C.) condenses the vaporous cyclopentadiene to a liquid, which flows from condenser 38 through line 42. A portion of the cyclopentadiene liquid flows back to distillation column 34 via line 44 as overhead reflux, and the remaining portion flows through line 46 to jacketed vessel 48. The contents of vessel 48 are cooled appropriately to prevent any possible dimerization of the cyclopentadiene. The liquid cyclopentadiene can be withdrawn from vessel 48 through line 50 as shown.

Figure 2:
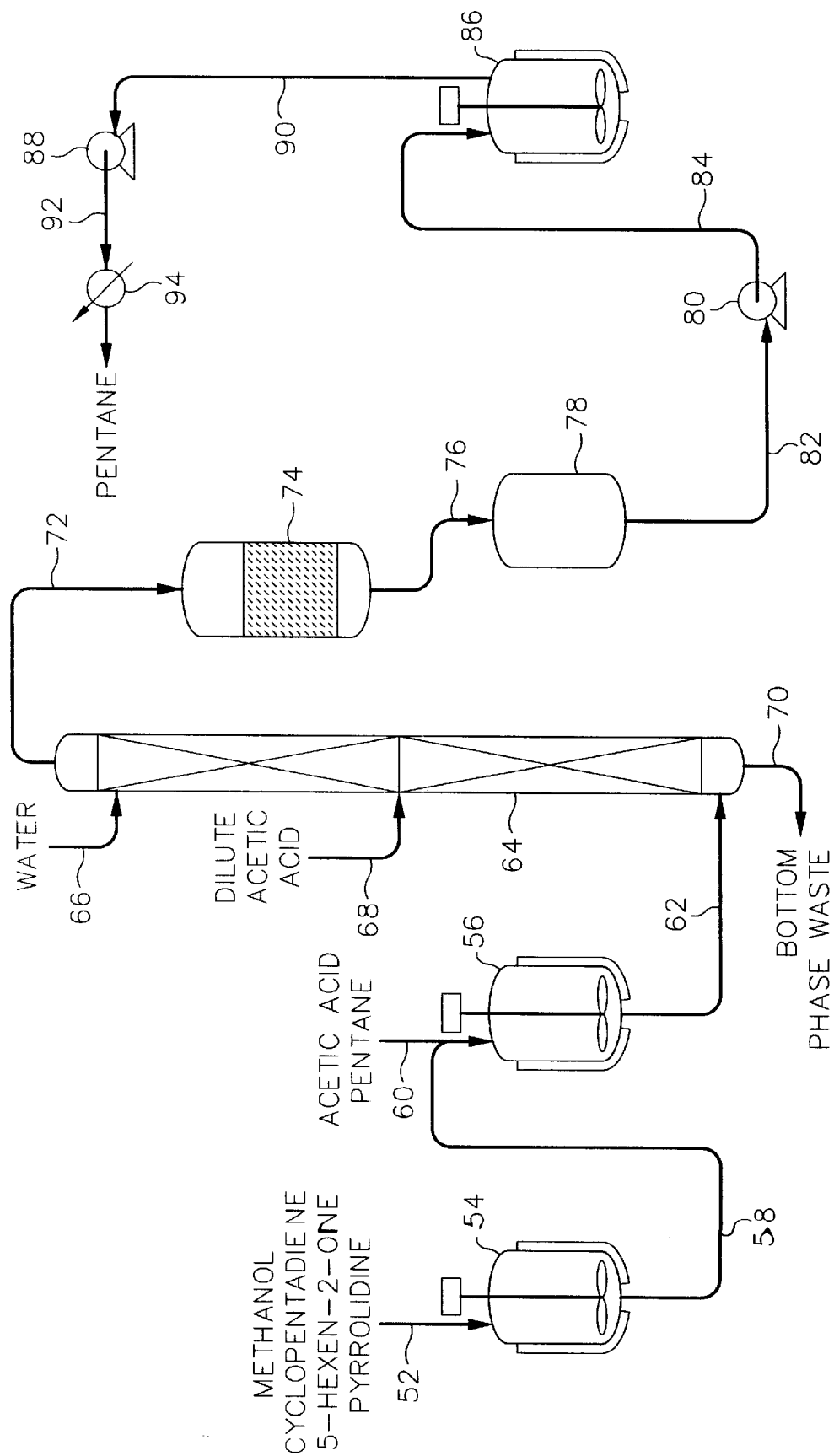

Referring to FIG. 2, 5-hexen-2-one (2.37 L) and methanol (5.00 L) are charged through line 52 to jacketed mixing vessel 54. The mixer for vessel 54 is started at 350 RPM, and vessel 54 is cooled to and maintained at 0° C. throughout mixing. Cyclopentadiene (1.90 L) is then charged to vessel 54, followed by pyrrolidine (1.00 L) which generates heat. During charging of the pyrrolidine, the temperature of vessel 54 is maintained at or below 15° C. Addition of the pyrrolidine requires about 1 hour to avoid overheating. After addition of all of the pyrrolidine, vessel 54 is heated to 20° C. and its contents are mixed for 1 hour to produce a mixture containing 6-but-3-enyl-6-methyl fulvene (resulting from the reaction of cyclopentadiene and 5-hexen-2-one), methanol, and pyrrolidine.

The mixture in vessel 54 is transferred to jacketed mixing vessel 56 via line 58 by pressurizing vessel 54 with nitrogen. The mixer of vessel 56 is started at 350 RPM, and such vessel is cooled to and maintained at 0° C. during mixing. Concentrated (99% weight percent aqueous solution) acetic acid (0.85 L) is charged through line 60 to vessel 56. As a result, heat is generated, and the temperature of vessel 56 is maintained at or below 15° C. during charging of acetic acid. This addition of acetic acid requires 30 minutes to prevent overheating. After all of the acetic acid is added, vessel 56 is heated to 20° C. and the contents are mixed at this temperature for 15 minutes. Pentane (5.0 L) is then charged to vessel 56, and mixing is continued at 350 RPM for 15 minutes. The resulting mixture contains methanol, 6-but-3-enyl-6-methyl fulvene as dissolved in pentane, and pyrrolidine acetate as resulting from the reaction of pyrrolidine and acetic acid.

Mixture from vessel 56 is introduced to the bottom of a water-containing extraction column 64 via line 62. Bottom and top liquid phases are established, as preferably enhanced by a coalescer pad (not shown). The bottom liquid phase contains pyrrolidine acetate and methanol as dissolved in water, and the top liquid phase contains 6-but-3-enyl-6-methyl fulvene as dissolved in pentane. An interface exists between the bottom and top liquid phases.

According to a continuous mode of operation, mixture from vessel 56 is passed continuously through line 62 to the bottom of extraction column 64, while at the same time water (preferably deionized) is passed continuously through line 66 to the top of extraction column 64, and dilute acetic acid (10–15 weight aqueous solution) is passed continuously through line 68 to the middle of extraction column 64. Suitable flow rates of mixture, water, and dilute acetic acid to the extraction column are established and maintained by flow control mechanisms which are not shown. The dilute acetic acid is employed to react with any small amounts of unreacted pyrrolidine which might be present in the extraction column. Extraction column 64 is maintained liquid-full and under pressure during operation with the interface between the phases being maintained at a predetermined level by a level controller (not shown). Bottom phase liquid flows continuously from the bottom of the extraction column through line 70 for disposal as waste. Top phase liquid flows continuously from the top of the extraction column through line 72 to silica filter 74. Silica filter 74 removes any small amounts of water and/or other impurities in the top phase liquid. The thus purified top phase liquid passes through line 76 and is collected in vessel 78. This continues until all of the mixture from vessel 56 is passed through extraction column 64.

Top phase liquid is pumped from vessel 78 by pump 80 so as to flow through line 82 and then through line 84 into jacketed mixing vessel 86. The mixer of vessel 86 is started at 350 RPM, and vessel 86 is cooled to and maintained at 10° C. As shown, vacuum pump 88 is in communication with vessel 86 through line 90. After starting vacuum pump 88, pentane is flashed from the top phase liquid in vessel 86, and the pentane vapor flows through line 90 to vacuum pump 88 and then through line 92 to condenser 94. Condenser 94 (set at 0° C.) condenses the pentane vapor to liquid. This procedure is continued until substantially all pentane is removed. The resulting, highly pure fulvene product consists essentially of 6-but-3-enyl-6-methyl fulvene. Vessel 86 is now cooled to and maintained at −10° C. until all the fulvene product is consumed in the next stage of the process shown in FIG. 3.

Figure 3:
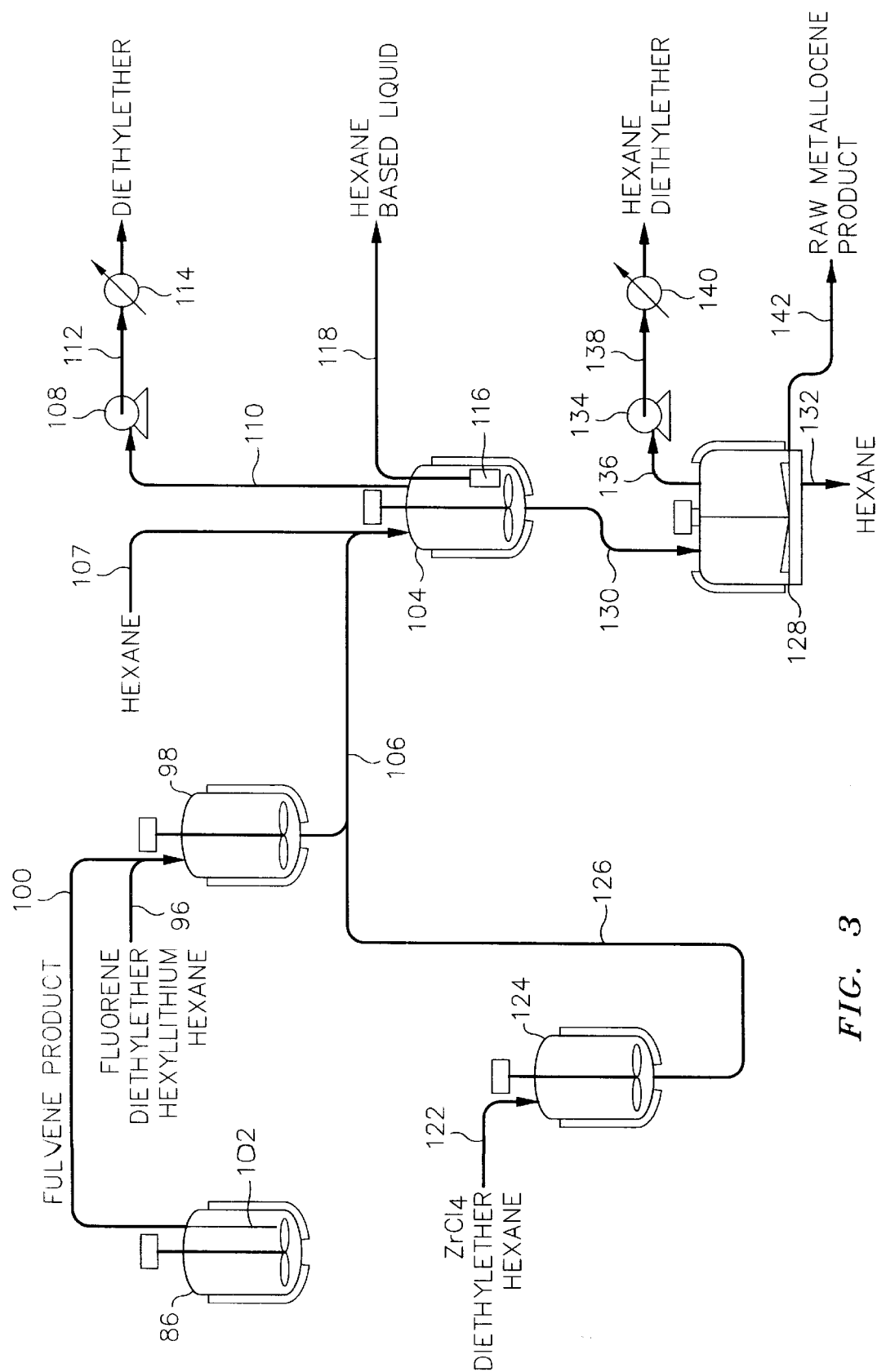

Referring to FIG. 3, solid fluorene (unsubstituted, 1.494 kg) is flushed through line 96 and into jacketed mixing vessel 98 with nitrogen. Diethylether (7.5 L) is charged through line 96 to vessel 98. The mixer of vessel 98 is started at 350 RPM, and vessel 98 is maintained at 25° C. during mixing. 2.28-M hexyllithium in hexane (4.05 L) is now charged through line 96 to vessel 98. Heat is generated, and the temperature of vessel 98 is maintained at or below 25° C. during charging of the hexyllithium. Addition of the hexyllithium requires 30 minutes to prevent overheating. Vessel 98 is now heated over a period of about 30 minutes to 35° C., followed by mixing for 1 hour and then cooling to 25° C. At this point, the mixture in vessel 98 contains fluorenyl-lithium.

Fulvene product (1.47 L) is transferred from vessel 86 (also shown in FIG. 2) to vessel 98 via line 100 by using dip-tube 102 and a flow of nitrogen to flush the fulvene product through line 100. Heat is generated when the fulvene product is added to vessel 98. The temperature is maintained at or below 25° C. during addition of fulvene product, which requires 30 minutes to prevent overheating. After addition of fulvene product is complete, mixing is carried out for 1 hour while maintaining vessel 98 at 25° C. At this point, the mixture in vessel 98 contains cyclopentadienyl-fluorenyl monolithium salt.

Additional 2.28-M hexyllithium in hexane (4.05 L) is charged through line 96 to vessel 98. Heat is generated in vessel 98. The temperature is maintained at or below 25° C. during charging of the hexyllithium, which requires 30 minutes to prevent overheating. Vessel 98 is now pressurized with nitrogen to 30 psig in order to transfer the mixture in vessel 98 to jacketed mixing vessel 104 via line 106. The mixer of vessel 104 is started at 350 RPM. Hexane (6.00 L) is now slowly charged through line 107 to vessel 104 over a period of about 1 hour to prevent phase separation. Vessel 104 is then set at a temperature of 20° C., followed by mixing for 30 minutes. The mixture in vessel 104 contains cyclopentadienyl-fluorenyl dilithium salt.

Vacuum pump 108 is in communication with vessel 104 through line 110. After starting vacuum pump 108, diethylether is flashed from the mixture in vessel 104, and the diethylether vapor flows through line 110 to vacuum pump 108, and then through line 112 to condenser 114. Condenser 114 (set at 0° C.) condenses the diethylether vapor to liquid. This procedure is continued until substantially all of the diethylether is evacuated as vapor from vessel 104. Vessel 104 is then cooled to 15° C. At this point, the dilithium salt has crystallized to result in a mixture having the dilithium salt as solids in a hexane-based liquid comprising hexane with any unreacted fluorene, hexyllithium, and 6-but-3-enyl-6-methyl fulvene dissolved therein. The mixer of vessel 104 is now stopped to lower a filter dip-tube 116 therein as shown. Vessel 104 is then pressurized with nitrogen to 30 psig to force most of the hexane-based liquid through the dip-tube and though line 118. After retracting dip-tube 116, fresh hexane (5 L) is charged through line 107 to vessel 104. The mixer is again started at 350 RPM, and vessel 104 is maintained at 15° C. The mixture in vessel 104 is now comprised of dilithium salt solids in hexane.

A slurried mixture of zirconium tetrachloride (2.12 kg) and hexane (6.00 L) is charged through line 122 to jacketed mixing vessel 124. The mixer of vessel 124 is started at 350 RPM, and vessel 124 is set at a temperature of 20° C. Diethylether (1.0 L) is charged through line 122 to vessel 124 to thereby generate heat. The temperature is maintained at or below 20° C. during charging of the diethylether, which requires 30 minutes to avoid overheating. Vessel 124 is then heated to 35° C., and mixing is continued for 1 hour. Vessel 124 is cooled to 15° C.

Vessel 124 is pressurized with nitrogen to a pressure of about 3 psig, and the pressure is slowly increased to a level that will start the flow of mixture from vessel 124 to vessel 104 via line 126. Heat is generated in vessel 104. The temperature is maintained at or below 20° C. during transfer of mixture from vessel 124 to vessel 104, which requires 15 minutes to prevent overheating. After the transfer is complete, vessel 124 is flushed with hexane (4.00 L) and then charged to vessel 104. Vessel 104 is heated to 30° C., and mixing at this temperature is carried out for 4 hours. Vessel 104 is then cooled to 20° C., and mixing is continued for 15 minutes at this temperature. The resulting mixture in vessel 104 contains a raw metallocene product (as solids) resulting from the reaction of the cyclopentadienyl-fluorenyl dilithium salt with the zirconium tetrachloride. The raw metallocene product comprises the metallocene 5-(cyclopentadienyl)-5-(9-fluorenyl)-1-hexene zirconium dichloride and also lithium chloride as a by-product.

Mixture in vessel 104 is transferred to jacketed "Nutsche" filter 128 via line 130 by means of pressurized nitrogen. This type of filter has a motor driven agitator and a 100 micron filter screen. Hexane is withdrawn as filtrate through line 132. Drying the remaining solids is carried out at a filter temperature of about 30° C. using vacuum pump 134 to flash any residual liquid hexane to vapor. Hexane vapor, as well as some diethylether vapor, flows through line 136 to vacuum pump 134 and then through line 138 to condenser 140 (set at 0° C.), which condenses the mixed vapor to liquid. The raw metallocene product is withdrawn from filter 128 through a suitable outlet port (not shown) and then through transfer line 142.

Figure 4:
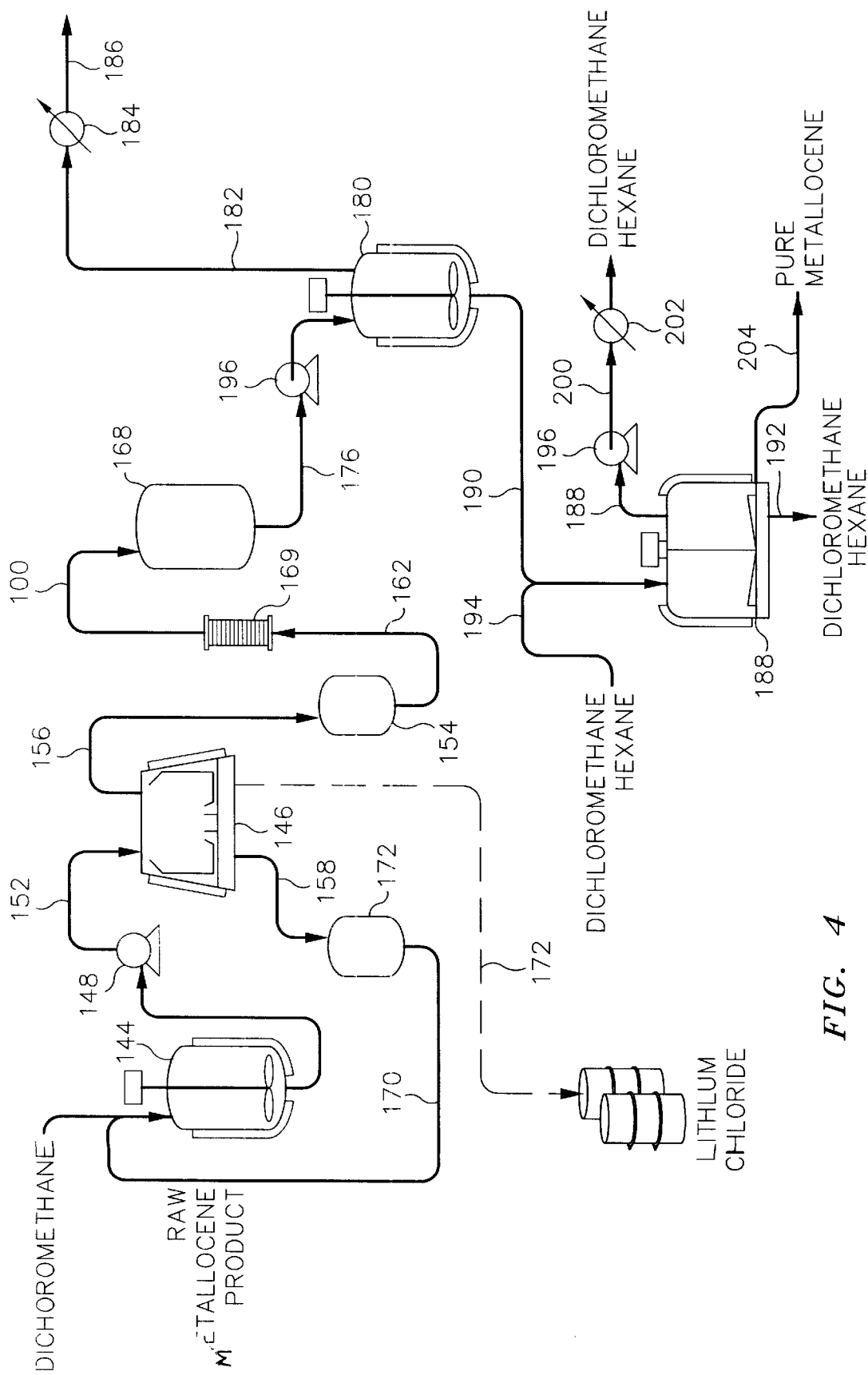

Referring to FIG. 4, raw metallocene product (1 kg) is flushed into jacketed mixing vessel 144 using nitrogen, and dichloromethane (20 L) is also charged into vessel 144. Vessel 144 is cooled to 0° C., and the contents therein are mixed at 350 RPM for 10 minutes. The metallocene dissolves in the dichloromethane to result in a metallocene solution. The lithium chloride is insoluble in the dichloromethane, so that a mixture is produced which comprises the metallocene solution and lithium chloride solids. Jacketed centrifuge 146 is purged with nitrogen for 20 minutes, and is then cooled to and maintained at 5° C. Centrifuge 146 is started slowly at first, and is increased in speed to preferably about 15,000 RPM. This results in a 20,000-G force on any material in the rotating bowl in the centrifuge.

The mixture of metallocene solution and lithium chloride solids in vessel 144 is pumped by pump 148 through lines 150 and 152 to centrifuge 146 at a predetermined rate. Metallocene solution, as the centrate, is collected in vessel 154 via line 156. Even though centrifuge 146 is cooled, some dichloromethane will flash in the bowl area and then condense. This liquid dichloromethane can be drained from centrifuge 146 through line 158 and into vessel 160. After all of the mixture has been fed from vessel 144 to centrifuge 146, pump 148 is stopped and the speed of the centrifuge is reduced to its normal resting state of 4000–5000 RPM.

Vessel 154 is pressurized with nitrogen to 20 psig so as to force the flow of metallocene solution through line 162, through metal filter 164, and through line 166 to vessel 168. Vessel 160 is similarly pressurized to cause the flow of dichloromethane through line 170 to vessel 144 for recycling. Centrifuge 146 is stopped and evacuated by any suitable means for 30 to 60 minutes to remove dichloromethane vapor. The bowl is removed from the centrifuge for removal of lithium chloride solids therefrom. The thus recovered lithium chloride is transferred to suitable containers as schematically indicated by the broken arrow at 172.

Metallocene solution in vessel 168 is pumped by pump 174 through lines 176 and 178 to jacketed mixing vessel 180. A second batch of raw metallocene product (1 kg) is processed as discussed above to result in refilling of vessel 168 with metallocene solution. The mixer of vessel 180 is started at 350 RPM, and vessel 180 is heated to 60° C. Liquid dichloromethane in the solution evaporates until the level of metallocene solution in vessel 180 drops to a predetermined level (typically about 60% fill). Dichloromethane vapor flows through line 182 to condenser 184. Condenser 184 (set at 0° C.) condenses the vapor back to a liquid, which flows through line 186 to a suitable storage vessel (not shown) for recycling. Additional batches of raw metallocene product can now be processed sequentially, with dichloromethane being recovered continuously, by operating pump 174 to maintain the desired level in vessel 180. The solution in vessel 180 becomes increasingly concentrated, and metallocene solids begin to crystallize out of the solution.

After all batches of raw metallocene product have been processed, the temperature of vessel 180 is reduced to 20° C., and the contents therein are mixed for 1 hour at 350 RPM. Vessel 180 is then cooled to −10° C. and the mixing is continued at such temperature for 4 hours to substantially complete crystallization of the metallocene.

Vessel 180 is then pressurized with nitrogen to 30 psig in order to transfer the mixture of dichloromethane and metallocene solids from vessel 180 to Nutsche filter 188 via line 190. The mixture is filtered by pressurizing filter 188 to 30 psig with nitrogen, thereby resulting in a flow of dichloromethane from filter 188 through line 192. Fresh dichloromethane (5 L) is charged through line 194 into filter 188 so as to wash the metallocene solids therein. This washing step is then repeated. Similarly, the metallocene solids in filter 188 are washed twice with fresh hexane (5 L). The metallocene solids are now dried by means of vacuum pump 196, which communicates with filter 188 through line 198. Operation of vacuum pump 196 flashes any residual dichloromethane and hexane liquids to vapors, which flow through line 198 to vacuum pump 196, and then through line 200 to condenser 202. Condenser 202 condenses the vapors to liquid dichloromethane and liquid hexane. Pure metallocene solids are withdrawn from filter 188 through line 204.

Obviously, many modifications and variations of the present invention are possible in light of the above teachings. It is, therefore, to be understood that within the scope of the appended claims, the invention may be practiced otherwise than as specifically described.

That which is claimed is:

1. A process for producing a bridged cyclopentadienyl-fluorenyl metallocene comprising:

(a) passing a dicyclopentadiene compound in liquid form into and through an evaporator under conditions conducive to the vaporization and cracking of the dicyclopentadiene compound, thereby producing a cyclopentadiene compound as a vapor;

(b) condensing the vaporous cyclopentadiene compound to a liquid;

(c) reacting, in a water-soluble alcohol and in the presence of an organic base, the liquid cyclopentadiene compound with a carbonyl compound selected from an aldehyde or a ketone to thereby produce a first mixture containing a fulvene compound;

(d) adding an acid and a first hydrocarbon to the first mixture, the acid being reactive with the organic base to produce a water-soluble salt and the fulvene compound being soluble in the first hydrocarbon to thereby result in a second mixture;

(e) passing second mixture to a water-containing extraction column to establish therein a bottom liquid phase, containing the water-soluble salt and alcohol as dissolved in the water, and a top liquid phase containing the fulvene compound as dissolved in the first hydrocarbon;

(f) withdrawing top liquid phase from the extraction column and separating the first hydrocarbon from the fulvene compound;

(g) reacting a fluorene compound with an alkali metal alkyl in a noncyclic ether, and then adding thereto the fulvene compound and additional alkali metal alkyl to produce a cyclopentadienyl-fluorenyl alkali metal salt in a resulting third mixture;

(h) providing a second hydrocarbon in the third mixture and separating the noncyclic ether therefrom to form a fourth mixture having the alkali metal salt as solids in a second hydrocarbon-based liquid comprising the second hydrocarbon with any unreacted fluorene, alkali metal alkyl, and fulvene compound dissolved therein, and then separating the second hydrocarbon-based liquid from the alkali metal salt solids;

(i) mixing the alkali metal salt solids with fresh second hydrocarbon and a zirconium, titanium, or hafnium tetrahalide compound so that the tetrahalide compound reacts with the alkali metal salt to produce a raw product comprising the bridged cyclopentadienyl-fluorenyl metallocene and an alkali metal halide as solids in the second hydrocarbon as a fifth mixture, and then separating the second hydrocarbon from the raw product;

(j) mixing the raw product with a halogenated organic solvent in which the metallocene is soluble and the alkali metal halide is insoluble, thereby producing a sixth mixture comprising a metallocene solution and the alkali metal halide solids; and (k) subjecting the sixth mixture to centrifuging so as to separate the alkali metal halide solids from the metallocene solution and then recovering the metallocene as solids from the metallocene solution.

2. A process as recited in claim 1 wherein the evaporator is a wiped film evaporator having an inner surface which is contacted by a plurality of rotating wipers.

3. A process as recited in claim 2 wherein the carbonyl compound is an olefinic carbonyl compound.

4. A process as recited in claim 3 wherein the carbonyl compound is 5-hexen-2-one and the fulvenyl compound is 6-but-3-enyl-6-methyl fulvene.

5. A process as recited in claim 1 wherein the water-soluble alcohol is methanol.

6. A process as recited in claim 5 wherein the organic base is a secondary amine.

7. A process as recited in claim 6 wherein the organic base is pyrrolidine.

8. A process as recited in claim 7 wherein the acid is acetic acid and the water-soluble salt is pyrrolidine acetate.

9. A process as recited in claim 8 wherein the first hydrocarbon is an alkane.

10. A process as recited in claim 9 wherein the first hydrocarbon is pentane.

11. A process as recited in claim 1 wherein steps (e) and (f) are carried out in a continuous manner during continuous passage of water into the extraction column and continuous withdrawal of bottom liquid phase from the extraction column until such time as all of the second mixture has been passed through the extraction column.

12. A process as recited in claim 4 wherein the fluorene compound is unsubstituted fluorene.

13. A process as recited in claim 1 wherein the alkali metal alkyl is hexyllithium.

14. A process as recited in claim 1 wherein the noncyclic ether is an alkyl ether.

15. A process as recited in claim 14 wherein the noncyclic ether is diethylether.

16. A process as recited in claim 13 wherein the second hydrocarbon is an alkane.

17. A process as recited in claim 16 wherein the second hydrocarbon is hexane.

18. A process as recited in claim 12 wherein the tetrahalide compound is zirconium tetrachloride and the metallocene is 5-(cyclopentadienyl)-5-(9-fluorenyl)-1-hexene zirconium dichloride.

19. A process as recited in claim 1 wherein the halogenated organic solvent is dichloromethane.

20. A process for producing and recovering a fulvene compound comprising:

reacting, in a water-soluble alcohol and in the presence of an organic base, a cyclopentadiene compound with a carbonyl compound selected from an aldehyde or a ketone to thereby produce a first mixture containing a fulvene compound;

adding an acid and a hydrocarbon to the first mixture, the acid being reactive with the base to produce a water-soluble salt and the fulvene compound being soluble in the hydrocarbon to thereby result in a second mixture;

passing second mixture to a water-containing extraction column to establish therein a bottom liquid phase, containing the water-soluble salt and alcohol as dissolved in the water, and a top liquid phase containing the fulvene compound as dissolved in the hydrocarbon; and withdrawing top liquid phase from the extraction column and separating the hydrocarbon from the fulvene compound.

21. A process as recited in claim 20 wherein the carbonyl compound is an olefinic carbonyl compound.

22. A process as recited in claim 21 wherein the carbonyl compound is 5-hexen-2-one and the filvene compound is 6-but-3-enyl-6-methyl fulvene.

23. A process as recited in claim 22 wherein the water-soluble alcohol is methanol.

24. A process as recited in claim 23 wherein the base is a secondary amine.

25. A process as recited in claim 24 wherein the base is pyrrolidine.

26. A process as recited in claim 25 wherein the acid is acetic acid and the water-soluble salt is pyrrolidine acetate.

27. A process as recited in claim 26 wherein the hydrocarbon is an alkane.

28. A process as recited in claim 27 wherein the hydrocarbon is pentane.

29. A process as recited in claim 20 wherein second mixture is passed to a water-containing extraction column and top phase liquid is withdrawn from the extraction column in a continuous manner during continuous passage of water into the extraction column and continuous withdrawal of bottom liquid phase from the extraction column until such time as all of the second mixture has been passed through the extraction column.

30. A process for producing a raw metallocene product comprising:

reacting a fluorene compound with an alkali metal alkyl in a noncyclic ether, and then adding thereto a fulvene compound and additional alkali metal alkyl to produce a cyclopentadienyl-fluorenyl alkali metal salt in a resulting first mixture;

providing a hydrocarbon in the first mixture and separating the noncyclic ether therefrom to form a second mixture having the alkali metal salt as solids in a hydrocarbon-based liquid comprising the hydrocarbon with any unreacted fluorene, alkali metal alkyl, and fulvene compound dissolved therein, and then separating the hydrocarbon-based liquid from the alkali metal salt solids; and mixing the alkali metal salt solids with fresh hydrocarbon and a zirconium, titanium, or hafnium tetrahalide compound so that the tetrahalide compound reacts with the alkali metal salt to produce the raw product comprising a bridged cyclopentadienyl-fluorenyl metallocene and an alkali metal halide as solids in the hydrocarbon as a third mixture, and then separating the hydrocarbon from the raw product.

31. A process as recited in claim 30 wherein the fluorene compound is unsubstituted fluorene.

32. A process as recited in claim 31 wherein the alkali metal alkyl is hexyllithium.

33. A process as recited in claim 31 wherein the noncyclic ether is an alkyl ether.

34. A process as recited in claim 33 wherein the noncyclic ether is diethylether.

35. A process as recited in claim 34 wherein the hydrocarbon is an alkane.

36. A process as recited in claim 35 wherein the hydrocarbon is hexane.

37. A process as recited in claim 31 wherein the fulvene compound is 6-but-3-enyl-6-methyl fulvene, the tetrahalide compound is zirconium tetrachloride, and the metallocene is 5-(cyclopentadienyl)-5-(9-fluorenyl)-1-hexene zirconium dichloride.

38. A process for recovering a metallocene from a raw product comprising the metallocene and an alkali metal halide as solids, comprising:

mixing the raw product with a halogenated organic solvent in which the metallocene is soluble and the alkali metal halide is insoluble, thereby producing a mixture comprising a metallocene solution and the alkali metal halide solids; and subjecting the mixture to centrifuging so as to separate the alkali metal halide solids from the metallocene solution and then recovering the metallocene as solids from the metallocene solution.

39. A process as recited in claim 38 wherein the halogenated organic solvent is dichloromethane.

40. A process as recited in claim 39 wherein the metallocene is 5-(cyclopentadienyl)-5-(9-fluorenyl)-1-hexene zirconium dichloride.

41. A process as recited in claim 40 wherein the alkali metal halide is lithium chloride.

42. A process for producing a bridged cyclopentadienyl fluorenyl metallocene by (1) passing dicyclopentadiene into a wiped film evaporator under conditions suitable for effecting cracking of the dicyclopentadiene to cyclopentadiene vapor, (2) distilling the reaction product and recovering cyclopentadiene, (3) reacting the recovered cyclopentadiene with a carbonyl compound selected from hydrocarbyl substituted ketones and hydrocarbyl substituted aldehydes in the presence of methanol and pyrrolidine to produce a 6-hydrocarbyl substituted fulvene, (4) adding a liquid alkane to the product of step (3) and subjecting the resulting mixture to separation in a liquid/liquid extraction column using water as the continuous phase, (5) recovering the 6-hydrocarbyl substituted fulvene from the alkane phase, (6) reacting a fluorene compound with an alkyl lithium in a liquid consisting essentially of non cyclic ether, alkane, or mixtures thereof to form the fluorenyl lithium salt, (7) adding the 6-hydrocarbyl substituted fulvene to the reaction mixture of step (6) to produce a lithium salt of an organic compound in which fluorenyl and cyclopentadienyl radicals are connected by a single carbon atom, (8) adding additional alkyl lithium to produce the dilithium salt of the organic compound, (9) forming a liquid mixture of a transition metal compound selected from the group consisting of the tetrahalides of Ti, Zr, and Hf by combining the transition metal compound with an liquid alkane and noncyclic ether,

(10) combining the liquid mixture with the product of step (7) to form the metallocene, and

(11) separating the metallocene from the reaction product.

\* \* \* \* \*